(12) United States Patent
Nozato

(10) Patent No.: US 9,044,174 B2
(45) Date of Patent: Jun. 2, 2015

(54) ADAPTIVE OPTICS APPARATUS, ADAPTIVE OPTICS METHOD, AND IMAGING APPARATUS

(75) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 111 days.

(21) Appl. No.: 12/945,447

(22) Filed: Nov. 12, 2010

(65) Prior Publication Data

US 2011/0116042 A1 May 19, 2011

(30) Foreign Application Priority Data

Nov. 17, 2009 (JP) ................................. 2009-262383

(51) Int. Cl.
*A61B 3/14* (2006.01)
*A61B 3/00* (2006.01)
*A61B 3/10* (2006.01)
*A61B 3/12* (2006.01)
*A61B 3/113* (2006.01)

(52) U.S. Cl.
CPC ............. *A61B 3/1225* (2013.01); *A61B 3/1015* (2013.01); *A61B 3/113* (2013.01); *A61B 3/102* (2013.01)

(58) Field of Classification Search
USPC .......... 351/200, 203, 205–206, 210–211, 221
See application file for complete search history.

(56) References Cited

U.S. PATENT DOCUMENTS

| 2003/0025874 A1* | 2/2003 | Williams et al. ............... 351/200 |
| 2007/0046948 A1* | 3/2007 | Podoleanu et al. ............ 356/497 |
| 2008/0033301 A1* | 2/2008 | DellaVecchia et al. ........ 600/477 |
| 2010/0149490 A1* | 6/2010 | Olivier et al. .................. 351/206 |

FOREIGN PATENT DOCUMENTS

| JP | 2006-006362 A | 1/2006 |
| JP | 2007515220 A | 6/2007 |
| JP | 2007330585 A | 12/2007 |
| JP | 2008161406 A | 7/2008 |
| JP | 2009-504294 A | 2/2009 |

OTHER PUBLICATIONS

Y.Zhang et al, "High-speed volumetric imaging of cone photoreceptors with adaptive optics spectral-domain optical coherence tomography", Optics Express, vol .14, No. 10, May 15, 2006.

(Continued)

*Primary Examiner* — Dawayne A Pinkney
(74) *Attorney, Agent, or Firm* — Canon U.S.A. Inc., IP Division

(57) ABSTRACT

An adaptive optics apparatus includes an aberration measuring unit that measures an aberration caused by a subject's eye, the aberration being measured on the basis of returning light that returns from the subject's eye; an aberration correcting unit that performs aberration correction in accordance with the aberration measured by the aberration measuring unit; an irradiation unit that irradiates the subject's eye with light corrected by the aberration correcting unit; and an adjusting unit that maintains a correction characteristic of the aberration correcting unit when the subject's eye moves out of a predetermined area.

43 Claims, 8 Drawing Sheets

(56) References Cited

OTHER PUBLICATIONS

Twisted-nematic liquid-crystal-on-silicon adaptive optics aberrometer and wavefront corrector, Seow-Hwang Eng et al, Jul. 27, 2009, XP040505938, Journal of Biomediacal Optics 14(4), 044014 (Jul./Aug. 2009).

High-speed volumetric imaging of cone photoreceptors with adaptive optics spectraldomain optical coherence tomography, XP009144793, Zhang Yan et al.
Indiana University AO-OCT System, XP009144825, Yan Zhang et al, Oct. 20, 2005.
Adaptive optics flood-illumination camera for high speed retinal imaging, XP009144824, May 15, 2006, Rha J et al.

* cited by examiner

ADAPTIVE OPTICS APPARATUS, ADAPTIVE OPTICS METHOD, AND IMAGING APPARATUS

BACKGROUND OF THE INVENTION

1. Field of the Invention

The present invention relates to an optical imaging method using an adaptive optics system and an optical imaging apparatus including the adaptive optics system. More particularly, the present invention relates to a method for obtaining a fundus image in which an aberration of a subject's eye is measured and corrected.

2. Description of the Related Art

Recently, scanning laser ophthalmoscopes (SLO) which two-dimensionally irradiate a fundus with a laser beam and receive light reflected by the fundus and imaging apparatuses using interference of low-coherence light have been developed as ophthalmologic imaging apparatuses.

The imaging apparatuses using the interference of low-coherence light is called optical coherence tomography (OCT) apparatuses, and is used, in particular, to obtain a tomographic image of a fundus or an area around the fundus.

Various types of OCT, such as time domain OCT (TD-OCT) and spectral domain OCT (SD-OCT), have been developed.

In the ophthalmologic imaging apparatuses, recently, the numerical aperture (NA) of the laser has been increased, and the resolution has been increased accordingly.

However, in the process of obtaining an image of a fundus, the fundus is irradiated with a laser beam through optical tissues, such as a cornea and a lens, of an eye.

As the resolution increases, the influence of an aberration of the cornea and the lens on the quality of the obtained image increases.

Accordingly, researches on adaptive optics SLO (AO-SLO) and adaptive optics OCT (AO-OCT) have been conducted. In AO-SLO and AO-OCT, an adaptive optics (AO) system, which is an adaptive optics system for measuring and correcting an aberration of the eye, is adopted. An example of AO-OCT is described in Optics Express, Vol. 14, No. 10, 15 May 2006, by Y. Zhang et al. In AO-SLO and AO-OCT, a wavefront of an eye is generally measured by a Shack-Hartmann wavefront sensor method.

In the Shack-Hartmann wavefront sensor method, the wavefront is measured by causing measurement light to be incident on the eye and receiving light reflected by the eye with a CCD camera through a microlens array. In AO-SLO and AO-OCT, a high-resolution image can be obtained by driving components such as a deformable mirror and a spatial phase modulator so as to correct the measured wavefront and obtaining an image of a fundus through the components. In an imaging apparatus including the above-described adaptive optics system according to the related art, feedback control is performed by repeating a process of measuring the aberration of the eye for correcting the aberration and a correcting process based on the measured aberrations.

The feedback control is performed to compensate for an error between a command value supplied to a correction device and an actual amount of correction and a variation in aberration caused in accordance with the state of lacrimal fluid and the state of refraction adjustment of the eye.

Similar to general feedback control, in the aberration correction control, it takes a certain time to establish a state in which the aberration is appropriately corrected after the control operation is started.

In particular, since response speeds of the wavefront sensor and a wavefront correction device used to correct the aberration are low, it takes several seconds to several tens of seconds to establish the state in which the aberration is appropriately corrected.

SUMMARY OF THE INVENTION

In an optical tomographic imaging apparatus, such as an OCT apparatus, that obtains an image of a fundus, it takes a relatively long time to complete an operation of obtaining an image of an eye after the operation is started. Therefore, there is a high possibility that the eye will temporarily move horizontally or vertically during the imaging operation.

In the case where the eye moves, it is useless to obtain an image of the eye since the imaging position is displaced from a desired position. Therefore, the imaging operation is resumed after the eye returns to the original position.

When the eye moves, a light path along which measurement light travels changes, and the measured aberration largely varies as a result.

Accordingly, in the aberration correction based on the above-described feedback control, the feedback control is performed so as to correct the aberration that has been varied, and the correction state changes from the original correction state.

Therefore, according to the related art, when the eye returns to the desired position, the time required to establish the state in which the aberration is appropriately corrected increases. Thus, it is difficult to quickly obtain an image of the fundus.

In light of the above-described situation, the present invention provides an optical imaging method using an adaptive optics system and an optical imaging apparatus including the adaptive optics system, the adaptive optics system being capable of reducing the time of feedback control required to appropriately correct an aberration when the position of a test object, which is an object of which an image is to be obtained, is moved. The present invention provides an optical imaging method using an adaptive optics system and an optical imaging apparatus including the adaptive optics system having the following structure.

An adaptive optics apparatus according to an aspect of the present invention includes an aberration measuring unit that measures an aberration caused by a subject's eye, the aberration being measured on the basis of returning light that returns from the subject's eye; an aberration correcting unit that performs aberration correction in accordance with the aberration measured by the aberration measuring unit; an irradiation unit that irradiates the subject's eye with light corrected by the aberration correcting unit; and an adjusting unit that maintains a correction characteristic of the aberration correcting unit when the subject's eye moves out of a predetermined area.

Further features of the present invention will become apparent from the following description of exemplary embodiments with reference to the attached drawings. Further features of the present invention will become apparent from the following description of exemplary embodiments with reference to the attached drawings.

DESCRIPTION OF THE EMBODIMENTS

Embodiments of the present invention will now be described. However, the present invention is not limited to the structures of the embodiments described below.

First Embodiment

An optical imaging apparatus and an optical imaging method in which an optical image of a test object is obtained by an SLO including an adaptive optics system according to a first embodiment of the present invention will be described with reference to FIG. 1.

According to the present embodiment, the test object, which is a measurement object, is an eye, and an image of a fundus of the eye is obtained by the optical imaging apparatus, which is the SLO, including the adaptive optics system. An eyepiece section of this apparatus is similar to that in an optical coherence tomography (OCT) apparatus.

Figure 1:
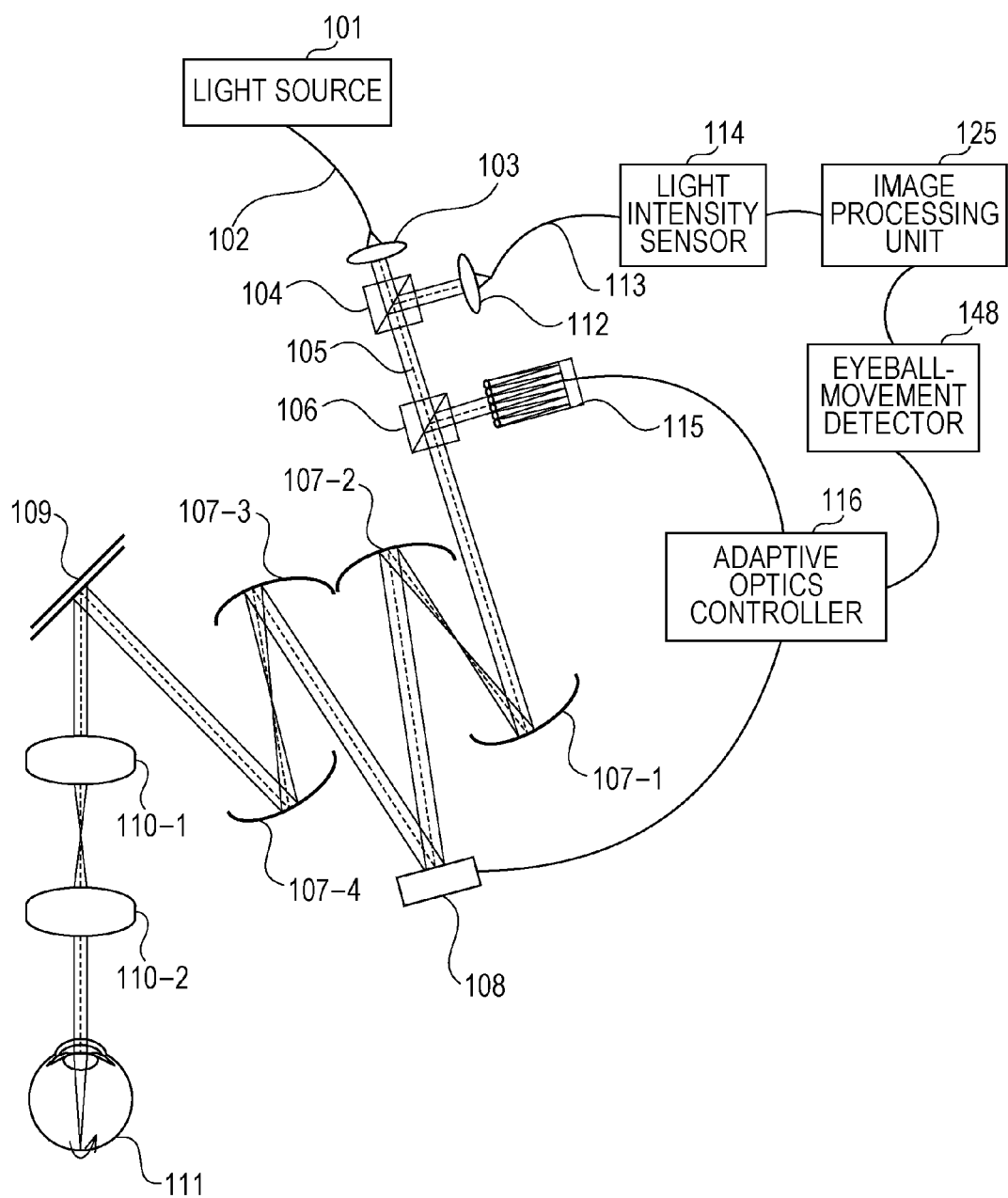
FIG. 1 is a schematic diagram illustrating the structure of an optical imaging apparatus including an SLO provided with an adaptive optics system according to a first embodiment of the present invention.

Referring to FIG. 1, in the present embodiment, a light source 101 is a superluminescent diode (SLD) with a wavelength of 840 nm.

The wavelength of the light source 101 is not particularly limited. However, in an apparatus for obtaining an image of a fundus, the wavelength can be set in the range of 800 nm to 1,500 nm to reduce glare for a subject and maintain the resolution.

Although the SLD is used in the present embodiment, a laser, for example, may instead be used.

In the case where the laser is used, a structure for reducing coherence, such as a long optical fiber, may be additionally used to reduce speckle noise.

In the present embodiment, a common light source is used for both obtaining the image of the fundus and measuring a wavefront. However, separate light sources may be used, and light rays from the respective light sources may be combined together at an intermediate position.

Light emitted from the light source 101 travels through a single-mode optical fiber 102, is collimated by a collimator 103, and is emitted as collimated light.

Measurement light 105 emitted from the collimator 103 passes through a beam splitter 104, which is a light splitting unit, and is guided to an adaptive optics system.

The adaptive optics system includes a beam splitter 106, which is a light splitting unit, a wavefront sensor (aberration measuring unit) 115, a wavefront correction device (aberration correcting unit) 108, and reflection mirrors 107-1 to 107-4.

The reflection mirrors 107-1 to 107-4 are arranged such that at least the pupil of the eye is optically conjugate with the wavefront sensor 115 and the wavefront correction device 108.

In the present embodiment, a deformable mirror is used as the wavefront correction device 108.

The deformable mirror is capable of locally changing a light reflection direction thereof. Various types of deformable mirrors are in practical use.

Figure 3A:
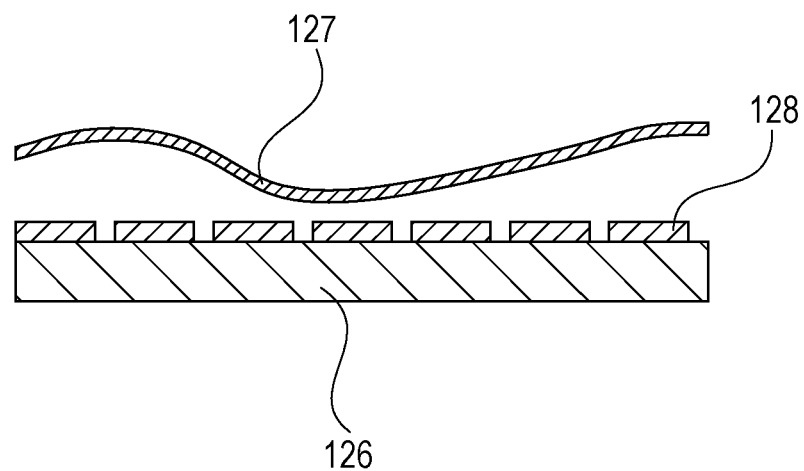
FIG. 3A is a schematic diagram illustrating a deformable mirror as an example of a wavefront correction device according to the first embodiment of the present invention.

For example, a device illustrated in FIG. 3A may be used as the wavefront correction device 108.

The device illustrated in FIG. 3A includes a film-shaped deformable mirror surface 127 that reflects incident light, a base portion 126, and actuators 128 disposed between the mirror surface 127 and the base portion 126.

With regard to the principle of operation of the actuators 128, the actuators 128 may be operated using electrostatic force, magnetic force, piezoelectric effect, etc., and the structure of the actuators 128 differs depending on the principle of operation thereof.

The actuators 128 are two-dimensionally arranged on the base portion 126, and are selectively driven so that the shape of the mirror surface 127 can be changed.

Figure 3B:
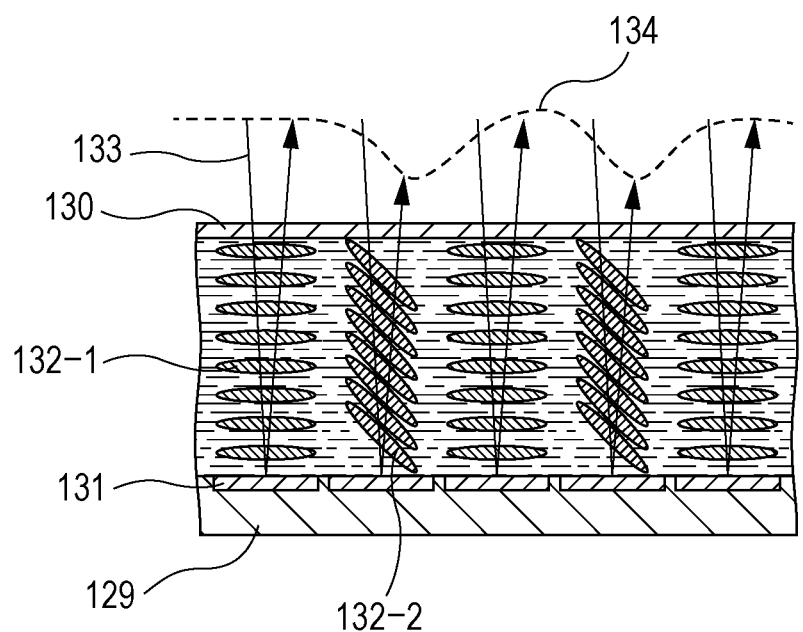
FIG. 3B is a schematic diagram illustrating a reflective liquid-crystal light modulator as another example of the wavefront correction device according to the first embodiment of the present invention.

A spatial phase modulator (reflective liquid-crystal light modulator) including a liquid crystal element illustrated in FIG. 3B is another example of the wavefront correction device 108.

This spatial phase modulator is structured such that liquid crystal molecules 132-1 and 132-2 are enclosed in a space surrounded by a base portion 129 and a cover 130.

A plurality of pixel electrodes 131 are provided on the base portion 129, and a transparent counter electrode (not shown) is provided on the cover 130.

When no voltage is applied between the electrodes, the liquid crystal molecules are oriented similarly to the liquid crystal molecules denoted by 132-1. When a voltage is applied, the liquid crystal molecules are oriented similarly to the liquid crystal molecules denoted by 132-2. Accordingly, the refractive index of the incident light changes in accordance with the orientation of the liquid crystal molecules.

The phase can be spatially modulated by changing the refractive index at each of the pixels by controlling the voltage applied to each of the pixel electrodes 131.

For example, in the case where light 133 is incident on the element, the phase of a light component that passes through the liquid crystal molecules 132-2 is delayed with respect to the phase of a light component that passes through the liquid crystal molecules 132-1. As a result, a wavefront 134 illustrated in FIG. 3B is formed.

Since the liquid crystal element has a polarization property, the liquid crystal element is generally provided with a polarizing plate or the like for adjusting the polarization of the incident light.

The light that has passed through the adaptive optics system is one-dimensionally or two-dimensionally scanned by a scanning optical system 109.

In the present embodiment, the scanning optical system 109 includes two galvano scanners for scanning the light in a main scanning direction (horizontal direction of the fundus) and a sub-scanning direction (vertical direction of the fundus). To achieve high-speed imaging operation, a resonance scanner may instead be used in the scanning optical system 109 for scanning the light in the main scanning direction.

Depending on the structure of the scanning optical system 109, an optical system including mirrors and lenses may be disposed between the scanners so as to set the scanners in the scanning optical system 109 to an optically conjugate state.

The measurement light scanned by the scanning optical system 109 is incident on an eye 111 through ocular lenses 110-1 and 110-2.

The measurement light incident on the eye 111 is reflected and diffused by the fundus.

The eye 111 can be appropriately irradiated with the measurement light in accordance with the visibility thereof by adjusting the positions of the ocular lenses 110-1 and 110-2.

Although lenses are included in the eyepiece section in the present embodiment, spherical mirrors or the like may be used instead.

The light reflected and diffused by a retina of the eye 111 travels in the reverse direction along the same path as the path along which the light has traveled to the eye 111, and is split by the beam splitter 106 such that a portion of the light is reflected toward the wavefront sensor 115 and is used to measure the wavefront of the light.

Figure 3C:
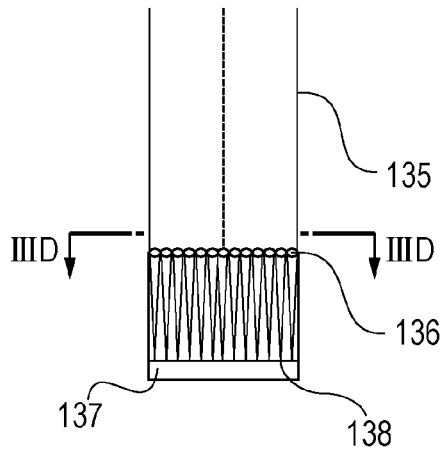
FIGS. 3C and 3D are schematic diagrams illustrating the structure of a Shack-Hartmann sensor as an example of a wavefront sensor according to the first embodiment of the present invention.
Figure 3D:
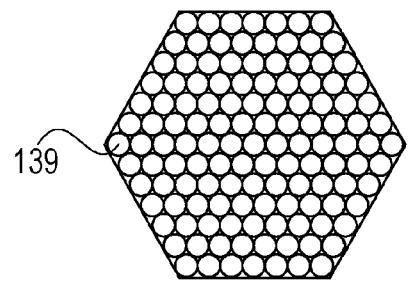

In the present embodiment, a Shack-Hartmann sensor illustrated in FIGS. 3C and 3D is used as the wavefront sensor 115.

Referring to FIG. 3C, the wavefront of a light ray 135 is measured. The light ray 135 is caused to pass through the microlens array 136, and is collected on a focal plane 138 of a CCD sensor 137. FIG. 3D is a sectional view of FIG. 3C taken along line IIID-IIID, which illustrates the structure of microlenses 139 included in the microlens array 136.

The light ray 135 is collected on the CCD sensor 137 through the microlenses 139. Therefore, the light ray 135 is collected at the same number of spots as the number of microlenses 139.

Figure 3E:
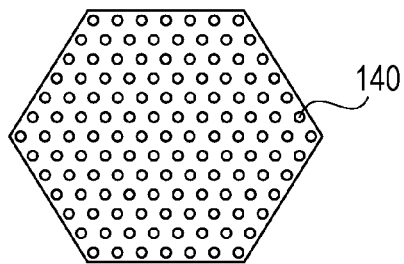
FIG. 3E is a schematic diagram illustrating the state in a light ray of which a wavefront is measured is collected on a CCD sensor according to the first embodiment of the present invention.

FIG. 3E illustrates the state in which the light ray 135 of which the wavefront is measured is collected on the CCD sensor 137. The light ray 135 passes through the microlenses 139 and is collected at spots 140.

Figure 3F:
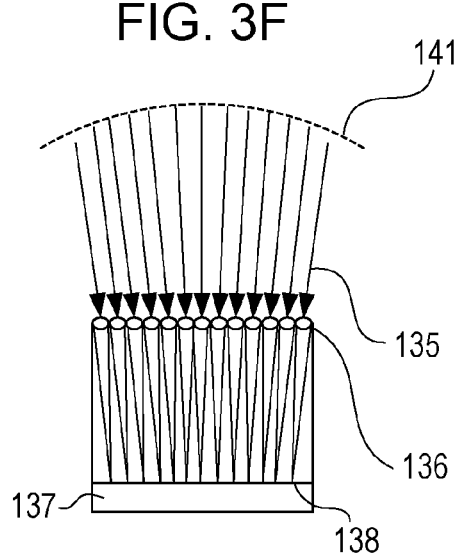
FIGS. 3F and 3G are schematic diagrams illustrating a case in which a wavefront having a spherical aberration is measured according to the first embodiment of the present invention.

The wavefront of the incident light ray 135 is calculated from the positions of the spots 140. For example, FIGS. 3F and 3G illustrate a case in which a wavefront having a spherical aberration is measured.

Here, it is assumed that the light ray 135 has a wavefront denoted by 141. The light ray 135 is collected by the microlens array 136 at positions corresponding to normal directions of local areas of the wavefront.

Figure 3G:
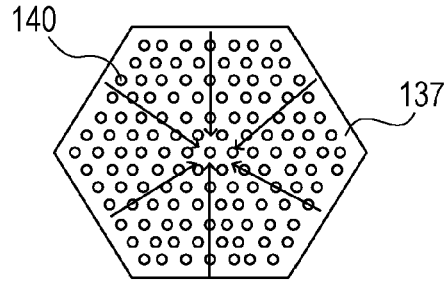

The state in which the light ray 135 is collected on the CCD sensor 137 in this case is illustrated in FIG. 3G.

Since the light ray 135 has a spherical aberration, the spots 140 are displaced toward the center. The wavefront of the light ray 135 can be determined by calculating the positions of the spots 140.

The reflected and diffused light that has passed through the beam splitter 106 is split by the beam splitter 104 such that a portion thereof is guided toward a photodetector 114 through a collimator 112 and an optical fiber 113. The light is converted into electric signals by the photodetector 114, and is reconstructed into a fundus image by an image processing unit 125.

In the first embodiment, an eyeball-movement detector 148 that detects a movement of the eye is provided as a position-variation detecting unit that detects a position variation of a test object by detecting a variation with time in an obtained image.

The structure of the eyeball-movement detector 148 is not limited to this. For example, the eyeball-movement detector 148 may directly detect a position variation of the eye.

The eyeball-movement detector 148 is connected to an adaptive optics controller 116, which is a control unit that performs feedback control of the wavefront correction device 108 for correcting the aberration caused in the eye.

The adaptive optics controller 116 determines that the feedback control of the wavefront correction device 108 is to be temporarily stopped on the basis of information of the eyeball movement obtained as a result of detection (measurement) performed by the eyeball-movement detector 148.

As other examples of the structure for detecting the movement of the eye, eyeball-movement detectors using a method of detecting a line of sight by irradiating the cornea with light (that is, a method of detecting a variation in the amount of light that returns from the cornea), a method of detecting the movement by measuring a specific position on the eye using an interferometer, etc., may be provided.

When these structures are used, the optical system of the eyepiece section is complex. However, it is not necessary to perform image processing for detecting the position, and therefore the process speed can be increased. In addition, the position detection accuracy can also be increased.

The wavefront sensor 115 is connected to the adaptive optics controller 116. The wavefront sensor 115 transmits the wavefront of the received light ray to the adaptive optics controller 116.

The wavefront correction device (deformable mirror) 108 is also connected to the adaptive optics controller 116. The deformable mirror 108 deforms into a shape specified by the adaptive optics controller 116.

The adaptive optics controller 116 calculates a shape with which the waveform can be corrected to a waveform without an aberration on the basis of the waveform transmitted from the wavefront sensor 115, and commands the deformable mirror 108 to deform into the calculated shape.

Feedback control is performed such that an optimum wavefront can be continuously formed by repeating the processes of measuring the wavefront with the wavefront sensor 115, transmitting the measured wavefront to the adaptive optics controller 116, and causing the adaptive optics controller 116 to command the deformable mirror 108 to correct the aberration.

In the present embodiment, if the eye temporarily moves during the imaging operation, the feedback control is temporarily stopped. Then, the feedback control is resumed when the eye returns to the original position. Accordingly, an image of the fundus can be obtained without a time loss.

More specifically, when the eyeball temporarily moves during the imaging operation, the eyeball-movement detector 148 detects a position variation of the eyeball, and informs the adaptive optics controller 116 that the position variation has occurred.

When the adaptive optics controller 116 is informed that the position variation has occurred (when a subject's eye moves out of a predetermined area, the adaptive optics controller 116 temporarily stops the feedback control while maintaining an aberration correction state at the time when the eye has started moving. Then, when the eye returns to the original position (when the eye moves into the predetermined area), the adaptive optics controller 116 resumes the feedback control from the maintained aberration correction state. The resuming of the feedback control means to make the correction on the basis of the amount of aberration determined before the movement of the subject's eye to the outside of the predetermined area. A determining unit that determines that the subject's eye has moved out of the predetermined area if the amount of aberration is lager than or equal to a predetermined value may be provided. When the amount of aberration returns from a value after the movement of the subject's eye to a value before the movement of the subject's eye, the determining unit can determine that the subject's eye has moved into the predetermined area.

Next, an aberration correction process performed by the adaptive optics system according to the present embodiment will be described with reference to FIGS. 4A to 4C.

Figure 4A:
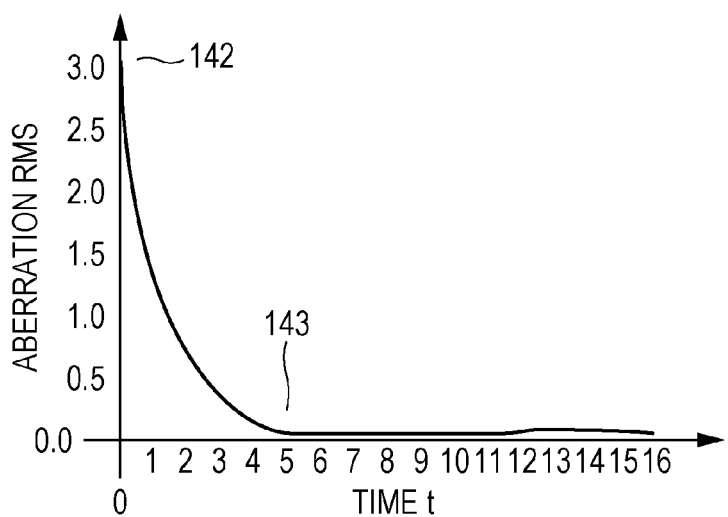
FIGS. 4A to 4C are graphs illustrating an aberration correction function provided by the adaptive optics system according to the first embodiment of the present invention.
Figure 4B:
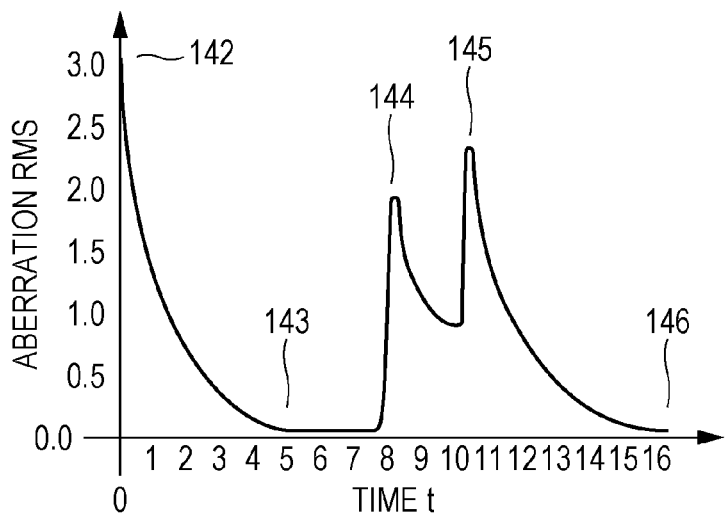
Figure 4C:
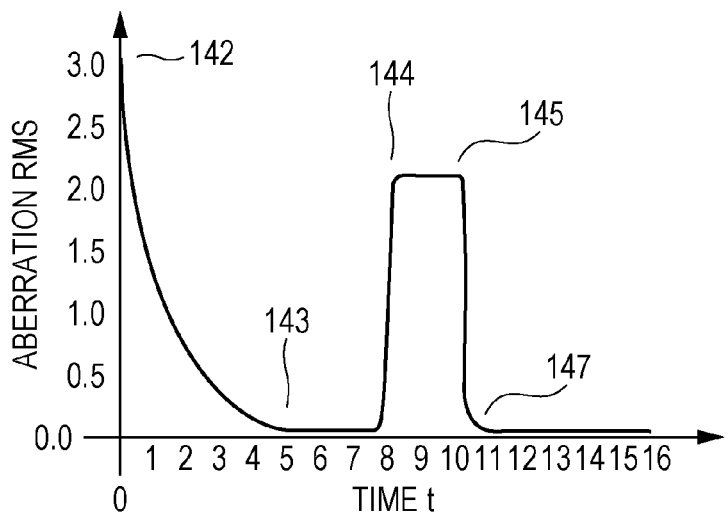

FIG. 4A illustrates the aberration correction effect obtained by a normal aberration correction function. The vertical axis shows the measured amount of aberration and the horizontal axis shows the time required to correct the aberration by the feedback control.

As denoted by 142, the amount of aberration is about 3 μm at the time when the aberration correction process is started.

The feedback control of the correction device is performed on the basis of the measured aberration, so that the aberration is gradually corrected. Accordingly, the aberration is substantially eliminated (that is, the amount of aberration is reduced to an amount that is smaller than or equal to a predetermined amount), as denoted by 143.

If the operation of obtaining a fundus image (for example, an OCT image) is performed at this time (at the time when the aberration is substantially eliminated), a high-resolution image can be obtained. Since the aberration is corrected by the feedback control as described above, it takes a several seconds to reduce the amount of aberration to an amount at which a high-resolution image can be obtained.

While the feedback control is being performed to correct the aberration, the amount of aberration is still large and it is difficult to obtain a high-resolution image.

Next, a variation in aberration caused in the structure of the related art when the eye, which is a test object, moves will be described with reference to FIG. 4B.

When the eye moves, the measured aberration largely varies and therefore the aberration correction system tries to correct the aberration that has been varied.

Similar to the above-described case, the aberration is initially large, as denoted by 142, and is reduced by the aberration correction process, as denoted by 143. Then, if the eye moves, the light path to the eye changes and therefore the aberration is greatly increased, as denoted by 144.

In the aberration correction process, the feedback control is performed to reduce this increased aberration, and accordingly the aberration is gradually reduced.

However, since the imaging position is moved from the intended position, it is useless to obtain an image of the fundus at this time. Therefore, the imaging operation is not performed.

Then, if the eye returns to the original position, the light path to the eye also returns to the original light path, and accordingly the aberration is increased again, as denoted by 145.

The feedback control is performed to reduce this increased aberration, and it takes a long time to substantially eliminate the aberration, as denoted by 146.

Since the eye is at the desired position at the time corresponding to the point denoted by 145, it is desirable to resume the imaging operation. However, a high-resolution image cannot be obtained for a certain time interval since the aberration is not yet eliminated.

Figure 5:
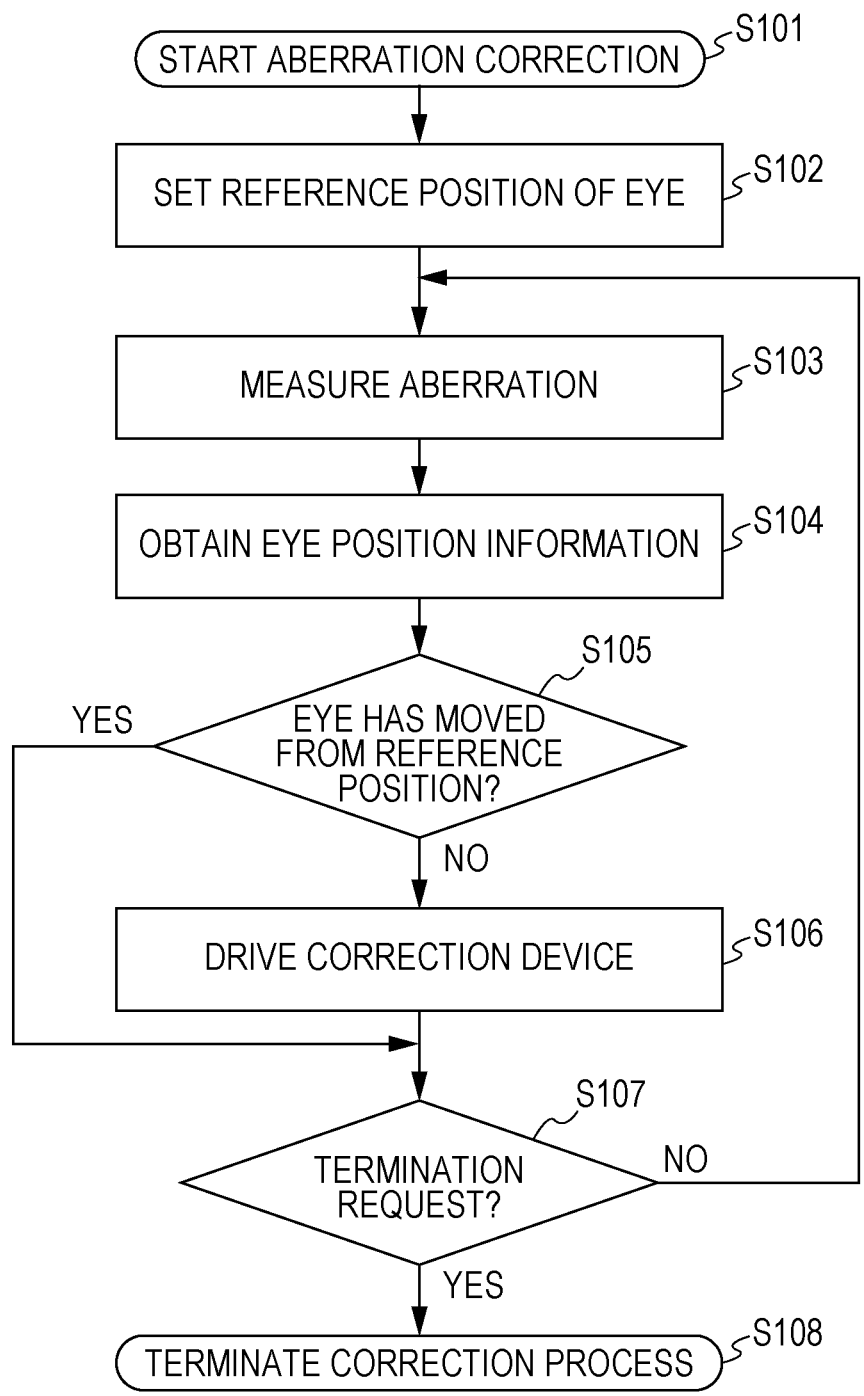
FIG. 5 is a flowchart illustrating an example of control steps according to the first embodiment of the present invention.

An example of the aberration correction process according to the present embodiment will be described with reference to FIG. 5.

First, the aberration correction process is started in step S101. Then, a reference position on the eye is set in step S102. The reference position is set to, for example, the position of a characteristic portion, such as a branching point of a blood vessel or an optic disc in the fundus image.

In step S103, the aberration is measured by the wavefront sensor 115. In step S104, the eyeball-movement detector 148 obtains eyeball position information.

In step S105, the eyeball-movement detector 148 determines whether or not the reference position of the eye has moved or whether or not the amount of movement of the reference position is small, and outputs the result of the determination to the adaptive optics controller 116. If it is determined that the eye has not moved or the amount of movement of the eye is small, the adaptive optics controller 116 drives the correction device on the basis of the aberration information in step S106.

If the eye has moved and is not at the desired position, the process proceeds to step S107 without performing steps S105 and S106. Therefore, the previous state of the correction device is maintained.

In step S107, it is determined whether or not a request for terminating the aberration correction process is issued. If the termination request is not issued, the process returns to step S103. If the termination request is issued, the process is terminated in step S108.

Figure 6:
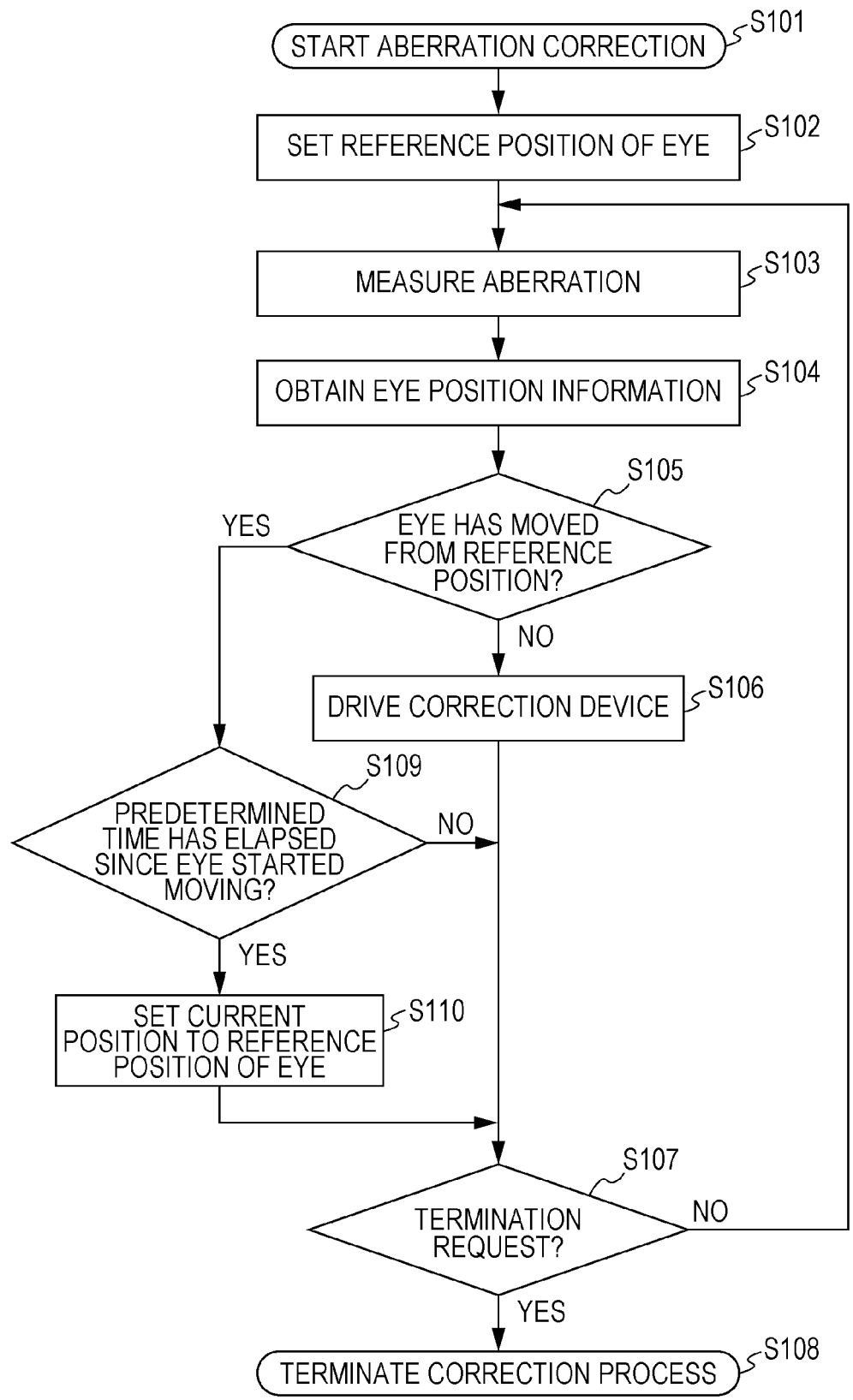
FIG. 6 is a flowchart illustrating another example of control steps according to the first embodiment of the present invention.

Another example of the aberration correction process will be described with reference to FIG. 6.

Similar to the above-described example, the aberration correction process is started in step S101.

Then, a reference position on the eye is set in step S102. In step S103, the aberration is measured by the wavefront sensor 115. In step S104, the eyeball-movement detector 148 obtains the eyeball position information.

In step S105, it is determined whether or not the eye has moved from the reference position. If the eye has not moved, the correction device is driven on the basis of the aberration information in step S106.

If the eye has moved, the process proceeds to step S109 and determines the time elapsed from when the eye started moving.

If the elapsed time is longer than or equal to a certain time (if the eye is displaced for a time longer than or equal to a predetermined time), it is determined that it is necessary to perform the imaging operation at the current position. Accordingly, the current position is set as the reference position of the eye in step S110.

Since the reference position is set to a new position, the aberration correction process is performed on the basis of the measured aberration from the next cycle.

Then, the process proceeds to step S107, where it is determined whether or not a request for terminating the process is issued. If the termination request is not issued, the process returns to step S103. If the termination request is issued, the process is terminated in step S108.

The manner in which the aberration correction state varies during the above-described process according to the present embodiment will be described with reference to FIG. 4C.

Similar to the above-described case, the aberration is initially large, as denoted by 142, and is reduced by the aberration correction process, as denoted by 143. Then, if the eye moves, the light path to the eye changes and therefore the aberration is greatly increased, as denoted by 144.

At this time, the eyeball-movement detector 148 detects the position variation of the eyeball and the adaptive optics controller 116 maintains the state of the correction device. Since the state of the correction device does not change, the amount of aberration is maintained at the amount at the point denoted by 144. However, this does not cause a problem since the imaging operation is not performed in this state.

The eye returns to the original position at the point denoted by 145. More specifically, the eyeball-movement detector 148 detects that the eye has returned to the original position (that is, that the eye is at the predetermined imaging position), and the adaptive optics controller 116 resumes the control of the correction device. At this time, the state of the correction device is substantially the same as the state in which the initial aberration can be corrected. Therefore, the aberration can be substantially eliminated in a very short time, as denoted by 147. As a result, a high-resolution image of the fundus can be obtained without a time loss.

Second Embodiment

An optical imaging apparatus and an optical imaging method in which an optical image is obtained by an OCT apparatus including an adaptive optics system according to a second embodiment of the present invention will be described with reference to FIG. 2.

Figure 2:
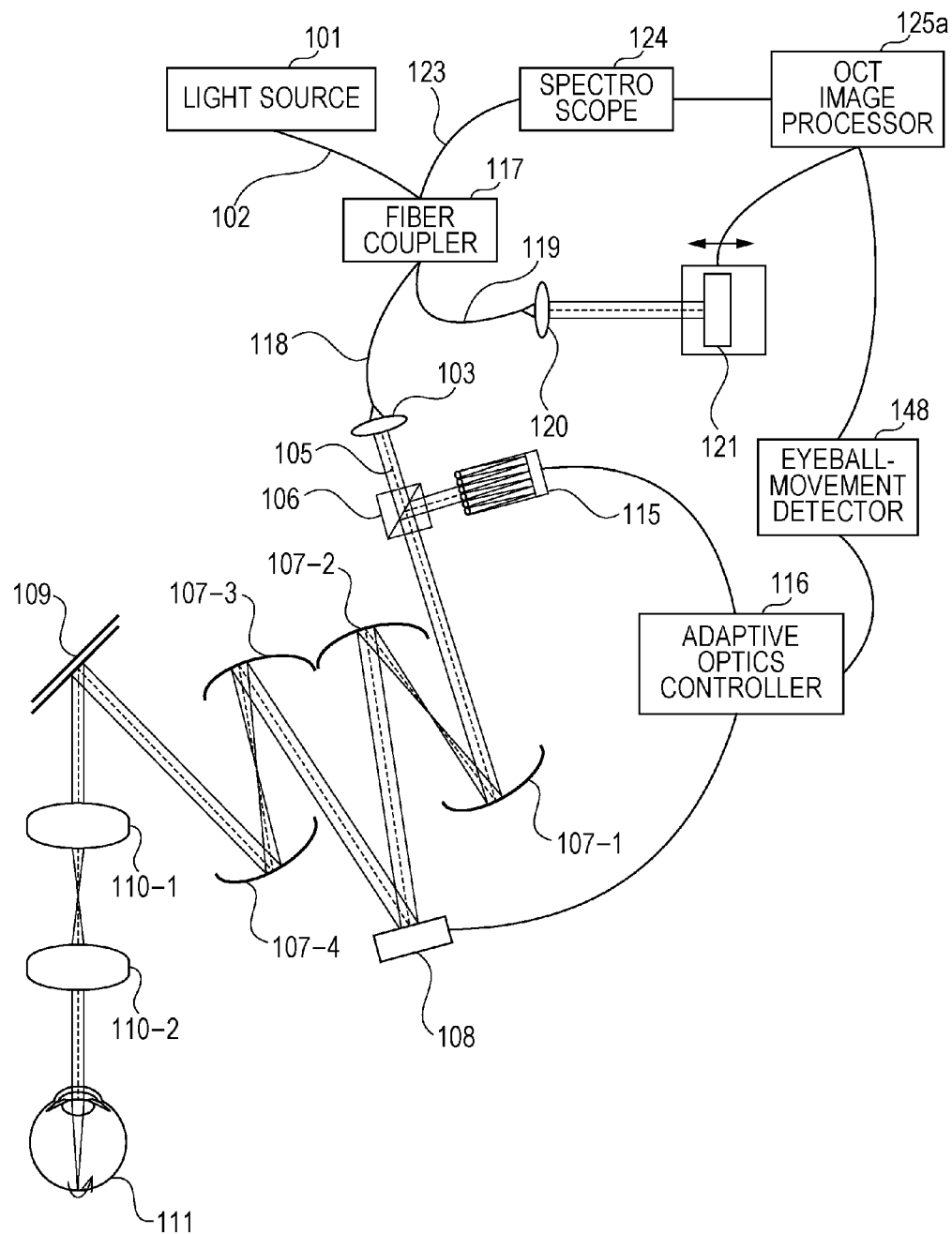
FIG. 2 is a schematic diagram illustrating the structure of an optical imaging apparatus including an OCT apparatus provided with an adaptive optics system according to a second embodiment of the present invention.

Referring to FIG. 2, in the present embodiment, a light source 101 is an SLD with a wavelength of 840 nm.

The light source 101 is not particularly limited as long as the light source 101 has a low coherence, and an SLD with a wavelength range of 30 nm or more can be used.

Alternatively, an ultrashort pulse laser, such as a titanium-sapphire laser, may be used as the light source 101.

Light emitted from the light source 101 travels through a single-mode optical fiber 102 and is guided to a fiber coupler 117. The fiber coupler 117 divides a path of the light into a signal light path 118 and a reference light path 119.

A branching ratio of the fiber coupler 117 is 10:90, and 10% of the light that reaches the fiber coupler 117 is caused to enter the signal light path 118.

The light that travels through the signal light path 118 is collimated by a collimator 103, and is emitted as collimated light. The section downstream of the collimator 103 is similar to that in the first embodiment. More specifically, the light passes through the adaptive optics system and the scanning optical system, and is incident on the eye 111. Then, light reflected and diffused by the eye 111 travels along the same path as the path along which the light has traveled to the eye 111, and is guided to the fiber coupler 117 through the signal light path (optical fiber) 118.

The reference light that travels through the reference light path 119 is emitted from a collimator 120, is reflected by a light-path-length changing unit 121 including a stage and a mirror mounted thereon, and returns to the fiber coupler 117.

The signal light and the reference light that reach the fiber coupler 117 are combined together. The combined light is guided to a spectroscope 124 through an optical fiber 123. A tomographic image of the fundus is formed by an OCT image processor 125a on the basis of interference light information obtained by the spectroscope 124.

The OCT image processor 125a controls the light-path-length changing unit 121 so that an image at a desired depth can be obtained.

The OCT image processor 125a is connected to an eyeball-movement detector 148. The eyeball-movement detector 148 is capable of detecting a movement of the eye by detecting a variation with time in the obtained image.

The eyeball-movement detector 148 is connected to an adaptive optics controller 116. The adaptive optics controller 116 controls the aberration correction process using the information of the detected eyeball movement.

According to the present embodiment, the optical imaging apparatus includes the OCT apparatus, and the image obtained by the OCT image processor 125a is three-dimensional data. Therefore, a three-dimensional movement of the eyeball can be detected.

The adaptive optics controller 116 performs a control operation similar to that in the first embodiment, so that a high-resolution tomographic image of the fundus can be obtained without a time loss even when the eye moves.

Third Embodiment

An optical imaging apparatus and an optical imaging method in which an optical image is obtained by an SLO including an adaptive optics system according to a third embodiment of the present invention will be described with reference to FIG. 7.

The basic structure of the present embodiment is similar to that of the first embodiment. The present embodiment differs from the first embodiment in that the eyeball-movement detector 148 is connected to the adaptive optics controller 116 but is not connected to the image processing unit 125.

Figure 7:
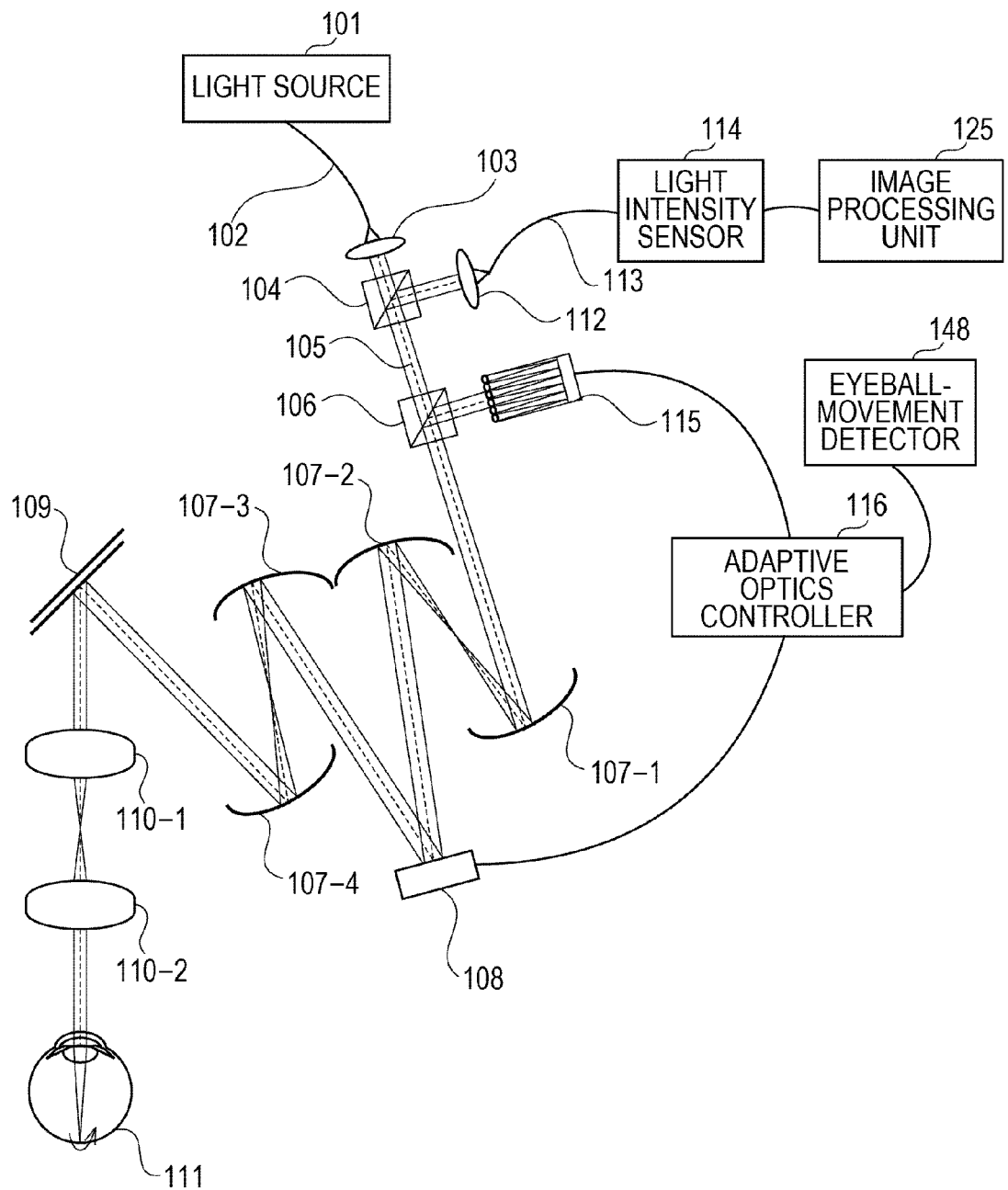
FIG. 7 is a schematic diagram illustrating the structure of an optical imaging apparatus, which is an SLO, including an adaptive optics system according to a third embodiment of the present invention.

Referring to FIG. 7, light emitted from the light source 101 is collimated by the collimator 103 and is guided to the eye 111 through the adaptive optics system and the eyepiece optical system, similar to the first embodiment.

Light reflected and diffused by the eye 111 travels in the reverse direction along the same path as the path along which the light has traveled to the eye 111, and is split by the beam splitter 106 such that a portion of the light is reflected toward the wavefront sensor 115 and is used to measure the wavefront of the light. The reflected and diffused light that has passed through the beam splitter 106 is split by the beam splitter 104 such that a portion thereof is reflected.

The reflected light is reflected and guided toward the photodetector 114 through the collimator 112 and the optical fiber 113.

The light is converted into electric signals by the photodetector 114, and is reconstructed into a fundus image by the image processing unit 125.

The wavefront sensor 115 is connected to the adaptive optics controller 116. The wavefront sensor 115 transmits the wavefront of the received light ray to the adaptive optics controller 116.

The deformable mirror 108 is also connected to the adaptive optics controller 116. The deformable mirror 108 deforms into a shape specified by the adaptive optics controller 116.

The adaptive optics controller 116 calculates a shape with which the waveform can be corrected to a waveform without an aberration on the basis of the waveform transmitted from the wavefront sensor 115, and commands the deformable mirror 108 to deform into the calculated shape.

Feedback control is performed such that an optimum wavefront can be continuously formed by repeating the processes of measuring the wavefront and commanding the deformable mirror to deform.

In the present embodiment, the eyeball-movement detector 148 detects the movement of the eyeball on the basis of the information obtained by the wavefront sensor 115, which is an aberration measuring unit.

As described above, when the eye moves by a large amount, the wavefront measured by the wavefront sensor 115 greatly varies. Therefore, the movement of the eyeball can be detected by monitoring the variation in the wavefront.

Similar to the first embodiment, when a movement of the eyeball is detected, the correction device is not driven and the shape thereof is maintained.

When the eye returns to the original position, it can be determined that the eyeball has returned to the original position since the wavefront measured by the wavefront sensor 115 also returns to the previously measured wavefront. When the eyeball returns to the original position, the adaptive optics controller 116 resumes the control of the correction device. At this time, the state of the correction device is substantially the same as the state in which the initial aberration can be corrected. Therefore, the aberration can be substantially eliminated in a very short time. As a result, a high-resolution image of the fundus can be obtained without a time loss.

As described above, according to the embodiments of the present invention, the optical imaging apparatuses including the SLO or the OCT apparatus may be structured as the imaging apparatuses for obtaining fundus images, and high-resolution images can be obtained even when the eye has an aberration.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262383 filed Nov. 17, 2009, which is hereby incorporated by reference herein in its entirety.

What is claimed is:

1. An adaptive optics apparatus comprising:
   an aberration measuring unit that measures an aberration of returning light that returns from a subject's eye irradiated with light;
   an aberration correcting unit that corrects at least one of an aberration of light and an aberration of returning light that returns from the subject's eye irradiated with light on the basis of the measured aberration;
   a detecting unit that detects whether or not the subject's eye moves out of a predetermined area; and
   a control unit that controls the aberration correcting unit so as to hold a correction characteristic of the aberration correcting unit at a current correction characteristic, in a case where the detecting unit detects that the subject's eye moves out of a predetermined area, the current correction characteristic being a characteristic used for correction by the aberration correcting unit when movement of the subject's eye out of the predetermined area is detected.

2. The adaptive optics apparatus according to claim 1, further comprising:
   a determining unit that determines that the subject's eye has moved out of the predetermined area in a case where an amount of the aberration is larger than or equal to a predetermined value.

3. The adaptive optics apparatus according to claim 2, wherein the determining unit determines that the subject's eye has returned into the predetermined area in a case where the amount of the aberration returns from a value after the movement of the subject's eye to a value before the movement of the subject's eye.

4. The adaptive optics apparatus according to claim 1, wherein
   the control unit performs feedback control of the aberration correcting unit on the basis of a measurement result obtained by the aberration measuring unit.

5. The adaptive optics apparatus according to claim 4, wherein the feedback control includes
   measuring a first aberration using first light from a light source,
   correcting an aberration of light that returns from the subject's eye irradiated with the second light, the aberration being corrected by controlling the aberration correcting unit on the basis of the first aberration,
   measuring a second aberration using the corrected light, and
   correcting an aberration of third light from the light source by controlling the aberration correcting unit on the basis of the second aberration.

6. The adaptive optics apparatus according to claim 4, wherein light used in the aberration measurement performed by the aberration measuring unit and light used to capture an image of the subject's eye are emitted from different light sources.

7. The adaptive optics apparatus according to claim 4,
   wherein the aberration correcting unit corrects an aberration of light that returns from the subject's eye irradiated with the light, and
   wherein the aberration measuring unit measures an aberration of the light corrected by the aberration correcting unit.

8. The adaptive optics apparatus according to claim 1,
   wherein the aberration is caused by an anterior segment of the subject's eye, and
   wherein the aberration correcting unit is disposed at a position where the aberration correcting unit is optically conjugate with the anterior segment of the subject's eye.

9. An imaging apparatus, comprising:
   the adaptive optics apparatus according to claim 1, the adaptive optics apparatus being used to form an image of the subject's eye; and
   an image capturing unit that captures the image of the subject's eye on the basis of returning light that returns from the subject's eye irradiated with the light.

10. The imaging apparatus according to claim 9, further comprising:
a separating unit that separates light from a light source into light to be incident on the aberration correcting unit and reference light,
wherein the image acquiring unit acquires a tomographic image of the subject's eye on the basis of interference light resulting from interference between the returning light that returns from the subject's eye irradiated with the light and the reference light.

11. The imaging apparatus according to claim 9, further comprising:
a detecting unit that detects a variation with time in the image,
wherein the control unit maintains the correction characteristic of the aberration correcting means in accordance with a result of the detection by the detecting unit.

12. The adaptive optics apparatus according to claim 1, further comprising:
a detecting unit that detects either a position of the subject's eye or a line of sight of the subject's eye,
wherein the control unit maintains the correction characteristic of the aberration correcting unit in accordance with a result of the detection by the detecting unit.

13. The adaptive optics apparatus according to claim 1, wherein the control unit controls the aberration correcting unit so as to restart, in a case where the detecting unit detects that the subject's eye returns into the predetermined area, correcting the at least one of an aberration of the light and an aberration of the returning light from the correction characteristic.

14. An adaptive optics method comprising:
an aberration measuring step of measuring an aberration of returning light that returns from a subject's eye irradiated with light;
an aberration correcting step of correcting at least one of an aberration of light and an aberration of returning light that returns from the subject's eye irradiated with light with an aberration correcting unit on the basis of the measured aberration;
a step of detecting whether or not the subject's eye moves out of a predetermined area; and
step of controlling the aberration correcting unit so as to hold a correction characteristic of the aberration correcting unit at a current correction characteristic, in a case where it is detected in the detecting step that the subject's eye moves out of a predetermined area, the current correction characteristic being that used for correction by the aberration correcting step when movement of the subject's eye out of the predetermined area is detected.

15. The adaptive optics method according to claim 14, wherein the aberration correcting unit is controlled so as to restart, in a case where it is detected that the subject's eye returns into the predetermined area, correcting the at least one of an aberration of the light and an aberration of the returning light from the correction characteristic.

16. An imaging apparatus comprising:
an aberration measuring unit that measures an aberration of returning light that returns from an object irradiated with light;
an aberration correcting unit that corrects at least one of an aberration of light and an aberration of returning light that returns from the object irradiated with light on the basis of the measured aberration; and
a unit that starts an operation of acquiring an image of the object in a case where an amount of the measured aberration is smaller than or equal to a predetermined value.

17. The imaging apparatus according to claim 16, wherein the unit starts the operation of acquiring a tomographic image of the object on the basis of interference light resulting from interference between returning light that returns from the object is irradiated with light and reference light.

18. The imaging apparatus according to claim 16, wherein the unit starts the operation of acquiring an image of the object while the aberration correcting unit corrects the aberration, in a case where the amount of measured aberration is smaller than or equal to the predetermined value.

19. The imaging apparatus according to claim 16,
wherein the object is a subject's eye, and
wherein the aberration correcting unit is arranged at a position optically conjugate with an anterior segment of the subject's eye.

20. An adaptive optics apparatus comprising:
an aberration measuring unit that measures an aberration of returning light that returns from a subject's eye irradiated with light;
an aberration correcting unit that corrects at least one of an aberration of light and an aberration of returning light that returns from the subject's eye irradiated with light on the basis of the measured aberration; and
a control unit that controls the aberration correcting unit so as to maintain, in a case where the subject's eye moves out of a predetermined area, a correction characteristic of the aberration correcting unit, and to restart, in a case where the subject's eye returns into the predetermined area, correcting the at least one of an aberration of the light and an aberration of the returning light from the correction characteristic.

21. An adaptive optics method comprising:
an aberration measuring step of measuring an aberration of returning light that returns from a subject's eye irradiated with light;
an aberration correcting step of correcting at least one of an aberration of light and an aberration of returning light that returns from the subject's eye irradiated with light with an aberration correction unit on the basis of the measured aberration; and
a control step of controlling the aberration correcting unit so as to maintain, in a case where the subject's eye moves out of a predetermined area, a correction characteristic of the aberration correcting unit, and to restart, in a case where the subject's eye returns into the predetermined area, correcting the at least one of an aberration of the light and an aberration of the returning light from the correction characteristic.

22. A non-transitory computer-readable storage medium including a program stored therein for executing an adaptive optics method, the adaptive optics method comprising:
an aberration measuring step of measuring an aberration of returning light that returns from a subject's eye irradiated with light;
an aberration correcting step of correcting at least one of an aberration of light and an aberration of returning light that returns from the subject's eye irradiated with light with an aberration correction unit on the basis of the measured aberration; and
a control step of controlling the aberration correcting unit so as to maintain, in a case where the subject's eye moves out of a predetermined area, a correction characteristic of the aberration correcting unit, and to restart, in a case where the subject's eye returns into the predetermined area, correcting the at least one of an aberration of the light and an aberration of the returning light from the correction characteristic.

23. A non-transitory computer-readable storage medium including a program stored therein for executing an adaptive optics method, the adaptive optics method comprising:
   an aberration measuring step of measuring an aberration of returning light that returns from a subject's eye irradiated with light;
   an aberration correcting step of correcting at least one of an aberration of light and an aberration of returning light that returns from the subject's eye irradiated with light with an aberration correcting unit on the basis of the measured aberration;
   a step of detecting whether or not the subject's eye moves out of a predetermined area; and
   a step of controlling the aberration correcting unit so as to hold a correction characteristic of the aberration correcting unit at a current characteristic, in a case where it is detected in the detecting step that the subject's eye moves out of a predetermined area, the current correction characteristic being that used for correction in the aberration correcting step when movement of the subject's eye out of the predetermined area is detected.

24. An imaging method comprising:
   an aberration measuring step of measuring an aberration of returning light that returns from an object irradiated with light;
   an aberration correcting step of correcting at least one of an aberration of light and an aberration of returning light that returns from the object irradiated with light on the basis of the measured aberration; and
   a step of starting an operation of acquiring an image of the object in a case where an amount of the measured aberration is smaller than or equal to a predetermined value.

25. The imaging method according to claim 24, wherein the operation of acquiring a tomographic image of the object is started on the basis of interference light resulting from interference between returning light that returns from the object irradiated with light and reference light.

26. The imaging method according to claim 24, wherein the operation of acquiring an image of the object is started while the aberration of corrected, in a case where the amount of measured aberration is smaller than or equal to the predetermined value.

27. The imaging method according to claim 24,
   wherein the object is a subject's eye, and
   wherein the aberration correcting unit is arranged at a position optically conjugate with an anterior segment of the subject's eye.

28. A non-transitory computer-readable storage medium including a program stored therein for executing an imaging method, the imaging method comprising:
   an aberration measuring step of measuring an aberration of returning light that returns from an object irradiated with light;
   an aberration correcting step of correcting at least one of an aberration of light and an aberration of returning light that returns from the object irradiated with light on the basis of the measured aberration; and
   an imaging-operation starting step of starting an operation of acquiring an image of the object in a case where an amount of the measured aberration is smaller than or equal to a predetermined value.

29. An imaging apparatus comprising:
   an aberration measuring unit that measures an aberration of returning light that returns from an object irradiated with light;
   an aberration correcting unit that corrects at least one of an aberration of light and an aberration of returning light that returns from the object irradiated with light on the basis of the measured aberration; and
   a control unit that that starts, in a case where an amount of aberration measured by the aberration measuring unit is smaller than or equal to a threshold value, an operation of capturing an image of the object while performing feed back control of the aberration correcting unit on the basis of a measurement result obtained by the aberration measuring unit.

30. The imaging apparatus according to claim 29, wherein the control unit starts the operation of capturing the image of the object by starting to construct the image of the object.

31. The imaging apparatus according to claim 29, wherein the control unit starts the operation of capturing the image of the object by starting to acquire the image of the object.

32. The imaging apparatus according to claim 29, further comprising:
   an acquiring unit that acquires a tomographic image of the object on the basis of interference light resulting from interference between returning light that returns from the object irradiated with measurement light and reference light corresponding to the measurement light,
   wherein the control unit controls the acquiring unit and starts the operation of capturing the image of the object while performing feedback control of the aberration correcting unit on the basis of a measurement result obtained by the aberration measuring unit.

33. The imaging apparatus according to claim 29,
   wherein the object is a subject's eye, and
   wherein the aberration correcting unit is arranged at a position optically conjugate with an anterior segment of the subject's eye.

34. An imaging apparatus comprising:
   a fundus imaging optical system that receives light reflected from a subject's eye and captures an image of a fundus of the subject's eye;
   a wavefront correcting device that is disposed in an optical path of the fundus imaging optical system, controls a wavefront of incident light and corrects a wavefront aberration of the subject's eye;
   a wavefront aberration detecting optical system that projects measurement light to the subject's eye and detect light reflected from the fundus with a wavefront sensor; and
   a control unit that performs feedback control of repeating detection of a wavefront aberration of the subject's eye on the basis of a detection signal from the wavefront sensor and control of the wavefront correcting device on the basis of a result of the detection, temporarily stops the feedback control on the basis of the detection signal from the wavefront sensor, and restarts the feedback control.

35. The imaging apparatus according to claim 34, wherein the control unit temporarily stops the feedback control and restarts the feedback control on the basis of information on a wavefront of reflected light detected by the wavefront sensor.

36. The imaging apparatus according to claim 34, wherein the control unit temporarily stops the feedback control and restarts the feedback control on the basis of a change in the wavefront of reflected light detected by the wavefront sensor.

37. The imaging apparatus according to claim 34, further comprising:
   a detecting unit that detects movement information about the subject's eye on the basis of a detection signal from the wavefront sensor,
   wherein the control unit temporarily stops the feedback control in a case where the movement information detected by the detecting unit is out of a predetermined range, and restarts the feedback control in a case where the movement information returns into the predetermined range.

38. The imaging apparatus according to claim 37, wherein the control unit reflects, on the wavefront correcting device, information on controlling the wavefront correcting device when the movement information is within the predetermined range, in a case where the movement information returns into the predetermined range.

39. A method of controlling an imaging apparatus including a wavefront correcting device that is disposed in an optical path of a fundus imaging optical system that receives light reflected from a subject's eye and captures an image of a fundus of the subject's eye, controls a wavefront of incident light and corrects a wavefront aberration of the subject's eye, and a wavefront aberration detecting optical system that projects measurement light to the subject's eye and detect light reflected from the fundus with a wavefront sensor, the method comprising:
performing feedback control of repeating detection of a wavefront aberration of the subject's eye on the basis of a detection signal from the wavefront sensor and control of the wavefront correcting device on the basis of a result of the detection; and
temporarily stopping the feedback control on the basis of the detection signal from the wavefront sensor, and restarting the feedback control.

40. A non-transitory computer-readable storage medium including a program stored therein for executing a method of controlling an imaging apparatus including a wavefront correcting device that is disposed in an optical path of a fundus imaging optical system that receives light reflected from a subject's eye and captures an image of a fundus of the subject's eye, controls a wavefront of incident light and corrects a wavefront aberration of the subject's eye, and a wavefront aberration detecting optical system that projects measurement light to the subject's eye and detect light reflected from the fundus with a wavefront sensor, the method comprising:
performing feedback control of repeating detection of a wavefront aberration of the subject's eye on the basis of a detection signal from the wavefront sensor and control of the wavefront correcting device on the basis of a result of the detection; and
temporarily stopping the feedback control on the basis of the detection signal from the wavefront sensor, and restarting the feedback control.

41. A method of controlling an imaging apparatus including an aberration measuring unit that measures an aberration of returning light that returns from an object irradiated with light and an aberration correcting unit that corrects at least one of an aberration of light and an aberration of returning light that returns from the object irradiated with light on the basis of the measured aberration, the method comprising:
starting, in a case where an amount of aberration measured by the aberration measuring unit is smaller than or equal to a threshold value, an operation of capturing an image of the object while performing feedback control of the aberration correcting unit on the basis of a measurement result obtained by the aberration measuring unit.

42. The method according to claim 41,
wherein the object is a subject's eye, and
wherein the aberration correcting unit is arranged at a position optically conjugate with an anterior segment of the subject's eye.

43. A non-transitory computer-readable storage medium including a program stored therein for executing a method of controlling an imaging apparatus including an aberration measuring unit that measures an aberration of returning light that returns from an object irradiated with light and an aberration correcting unit that corrects at least one of an aberration of light and an aberration of returning light that returns from the object irradiated with light on the basis of the measured aberration, the method comprising:
starting, in a case where an amount of aberration measured by the aberration measuring unit is smaller than or equal to a threshold value, an operation of capturing an image of the object while performing feedback control of the aberration correcting unit on the basis of a measurement result obtained by the aberration measuring unit.

\* \* \* \* \*